US005617865A

United States Patent [19]

Palczewska et al.

[11] Patent Number: 5,617,865

[45] Date of Patent: Apr. 8, 1997

[54] MULTI-DIMENSIONAL ULTRASONIC ARRAY INTERCONNECT

[75] Inventors: Grazyna Palczewska; Ron Ho, both of Seattle, Wash.

[73] Assignee: Siemens Medical Systems, Inc., Iselin, N.J.

[21] Appl. No.: 414,980

[22] Filed: Mar. 31, 1995

[51] Int. Cl.$^6$ .............................. A61B 8/00; H04R 17/00

[52] U.S. Cl. ...................................... 128/662.03; 29/25.35

[58] Field of Search ........................ 128/661.01, 660.01, 128/662.03, 663.01; 310/334; 29/25.35

[56] References Cited

U.S. PATENT DOCUMENTS

| | | | |
|---|---|---|---|
| 5,091,893 | 2/1992 | Smith et al. | 367/153 |
| 5,320,104 | 6/1994 | Fearnside et al. | 128/661.01 |
| 5,359,760 | 11/1994 | Busse et al. | 29/25.35 |
| 5,402,793 | 4/1995 | Gruner et al. | 128/660.1 |
| 5,438,998 | 8/1995 | Hanafy | 128/662.03 |
| 5,493,541 | 2/1996 | Snyder | 367/155 |

FOREIGN PATENT DOCUMENTS

| | | |
|---|---|---|
| 0212737 | 3/1987 | European Pat. Off. . |
| 4-22347 | 1/1992 | Japan . |

OTHER PUBLICATIONS

"Two-Dimensional Array Transducers Using Thick Film Connection Technology," Stephen W. Smith, IEEE Transactions on Ultrasonics, Ferroelectrics, and Frequency Control, vol. 40, No. 6, pp. 727–734, Nov. 1993.

"Fabrication and Characterization of Transducer Elements in Two-Dimensional Arrays for Medical Ultrasonic Imaging," Daniel H. Turnbull and F. Stuart Foster, IEEE Transactions on Ultrasonics, Ferroelectrics, and Frequency Control, vol. 39, No. 4, pp. 464–475, Jul. 1992.

"Expanding-Aperture Annular Array," D.R. Dietz, S.I. Parks, and M. Linzer, Ultrasonic Imaging, vol. 1, No. 1, pp. 56–75, 1979.

"Further Development and Clinical Evaluation of the Expanding Aperture Annular Array System," S.I. Parks, M. Linzer, and T.H. Shawker, Note (journal uncertain—Academic Press, Inc.) pp. 378–383, 1979.

"Relaxor Ferroelectric Transducers," H. Takeuchi, H. Masuzawa, C. Nakaya, and Y. Ito, 1990 Ultrasonics Symposium (IEEE), pp. 697–705, 1990.

*Primary Examiner*—Francis Jaworski

*Attorney, Agent, or Firm*—Jeffrey Slusher

[57] ABSTRACT

An ultrasonic transducer array has a piezoelectric ceramic layer that is separated in a longitudinal direction into n transducer groups. Each group is separated in a transverse direction into m elements. A double-sided flex circuit has a flexible, non-conductive base layer, through which conductive vias extend and are in electrical contact with a respective element. A conductive layer on a bottom side of the flex circuit is divided into a plurality of electrodes, each of which is in electrical contact with a respective one of the elements. For each group, electrically conductive traces connect predetermined ones of the flex circuit electrodes with external driving circuitry, and are located on a top side of the flex circuit. Transducer groups with different numbers of elements are provided, some with 1.5-D operation (with element pairs stimulated via a common trace) and some with 2-D operation (with separate traces for each element). For embodiments with more than three elements per group, the flex circuit includes more than one base layer. The invention also makes it possible at most two traces located on the top side of the flex circuit for each group, measured in the longitudinal direction. In one implementation, each array group was no wider than 300 μm, each trace was at least 50 μm, and the separation between each via and the nearest trace which is not connected to it was at least 75 μm.

7 Claims, 2 Drawing Sheets

FIG. 3
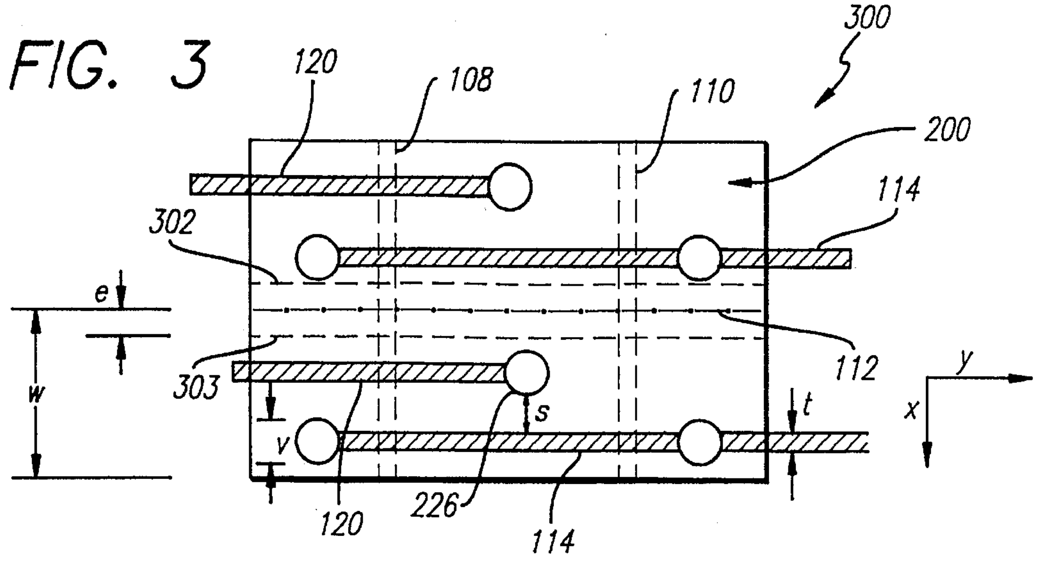
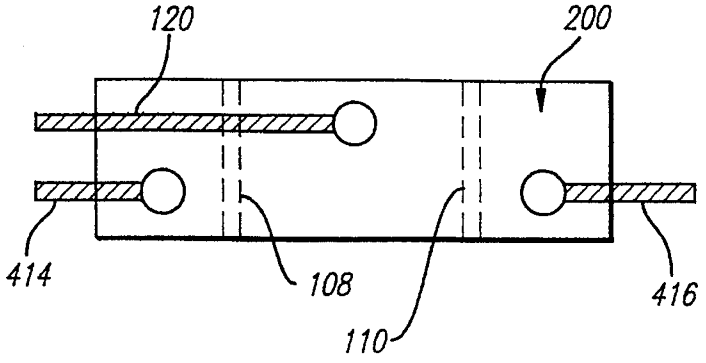
FIG. 4
FIG. 5
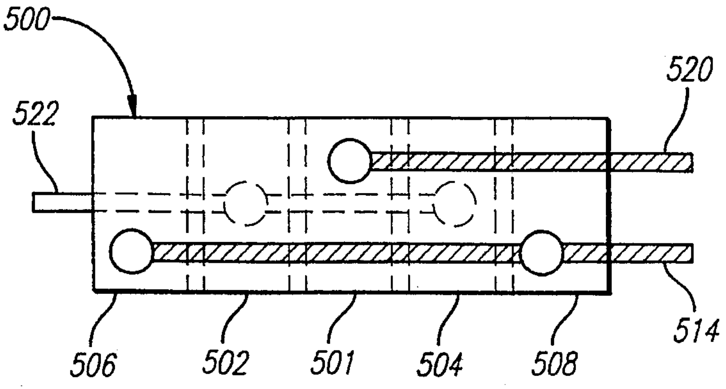
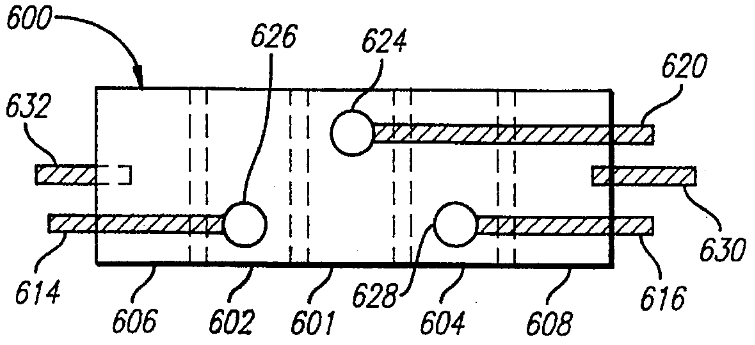
FIG. 6

MULTI-DIMENSIONAL ULTRASONIC ARRAY INTERCONNECT

BACKGROUND OF THE INVENTION

1. Field of the Invention

This invention relates to a structure for ultrasonic arrays such as those used in transducers for medical imaging, and in particular to the electrical interconnections of the array elements.

2. Description of the Related Art

In the area of medical imaging, there are the standing goals of making the transducers ever smaller, and of designing transducers that have greater resolution and flexibility, such as the ability to change the aperture. In order to achieve both goals, one must be able to form ever more transducer elements within a given space. The problem then arises that it is also necessary to electrically connect each element to the driving circuitry and, in many cases, to one another. These interconnections also take up space, and also limit how small a transducer element can be.

Interconnection problems are particularly troublesome in multi-dimensional arrays, which are often used to provide variable apertures or focus. For example, in an array that is three elements wide and 128 elements long, in each group of three elements, one element will be between the other two, so that an electrical conductor must be arranged so that it leads to the "middle" element without interfering with the two adjacent outer elements. Providing the necessary interconnects in such arrays often requires complicated, sensitive, and expensive fabrication procedures.

The following references all describe known array structures and fabrication techniques that attempt to address these problems:

1) "Two-Dimensional Array Transducers Using Thick Film Connection Technology," Stephen W. Smith, IEEE Transactions on Ultrasonics, Ferroelectrics, and Frequency Control, Vol. 40, No. 6, pp. 727–34, November 1993;

2) "Fabrication and Characterization of Transducer Elements in Two-Dimensional Arrays for Medical Ultrasonic Imaging," Daniel H. Turnbull and F. Stuart Foster, IEEE Transactions on Ultrasonics, Ferroelectrics, and Frequency Control, Vol. 39, No. 4, pp. 464–75, July 1992; and 3) European Patent Application 0 212 737 (Inventor: 't Hoen, 4 March 1987).

What is needed is an array structure that makes possible either smaller elements in a multi-dimensional ultrasonic transducer array, a more easily fabricated array, or both, with an efficient and easily implemented interconnection arrangement.

SUMMARY OF THE INVENTION

An ultrasonic transducer array has a piezoelectric ceramic layer that is separated in a longitudinal direction into n transducer groups. Each group is in turn separated in a transverse direction into m transducer elements.

The transducer also includes a double-sided flex circuit that comprises a flexible, electrically non-conductive base layer, through which electrically conductive vias extend and are in electrical contact with a respective transducer element. An electrically conductive layer on a bottom side of the flex circuit is divided into a plurality of flex circuit electrodes, each of which is in electrical contact with a respective one of the transducer elements. For each group, electrically conductive traces are electrically connected to predetermined ones of the flex circuit electrodes and to external driving circuitry, and are located on a top side of the flex circuit.

In one embodiment of the invention, each transducer group has three elements—a center element and two outer elements, and the two outer elements are electrically connected by a single trace. In a selectable 1.5-D or 2-D embodiment, there is a separate trace for each element and each of the three elements is electrically connected to and independently stimulated over its respective trace.

The invention also provides a transducer with more than three elements to a group. In these embodiments, the flex circuit includes more than one flexible, electrically non-conductive base layers. The electrically conductive vias thereby extend through all the base layers and are in electrical contact with the respective transducer element. The electrically conductive traces are located on a top surface of each base layer.

In one five-element wide embodiment, each transducer group has—a center element, two intermediate elements, and two outer elements. Separate traces are provided for the center element and the outer elements of each group but vias are provided only for the center element and the intermediate elements. The outer elements have separate traces that directly connect the flex circuit electrodes for the outer elements with the external circuitry and are located entirely off of the top surface of the base layer. Each of the five elements in each group is thereby provided for independent stimulation over a respective trace.

Although it is not necessary, the invention makes it possible to have no more than two traces located on the top side of the flex circuit for each group, measured in the longitudinal direction. In one actual prototype, this made it possible to implement an array in which each array group was no wider than 300 μm, each trace was at least 50 μm, and the separation between each via and the nearest trace which is not connected to it was at least 75 μm.

BRIEF DESCRIPTION OF THE DRAWINGS

FIG. 3 shows a top view of the transducer according to the invention with the backing layer removed.

FIG. 4 illustrates a group of array elements in a selectable 1.5- or 2-dimensional 3×n array with independent electrical leads for each element.

FIG. 5 illustrates a double flex layer, 5×n, 1.5-D embodiment of the invention.

FIG. 6 illustrates a group of array elements in a selectable 1.5- or 2-dimensional 5×n array with independent electrical leads for each element.

DETAILED DESCRIPTION

Figure 1:
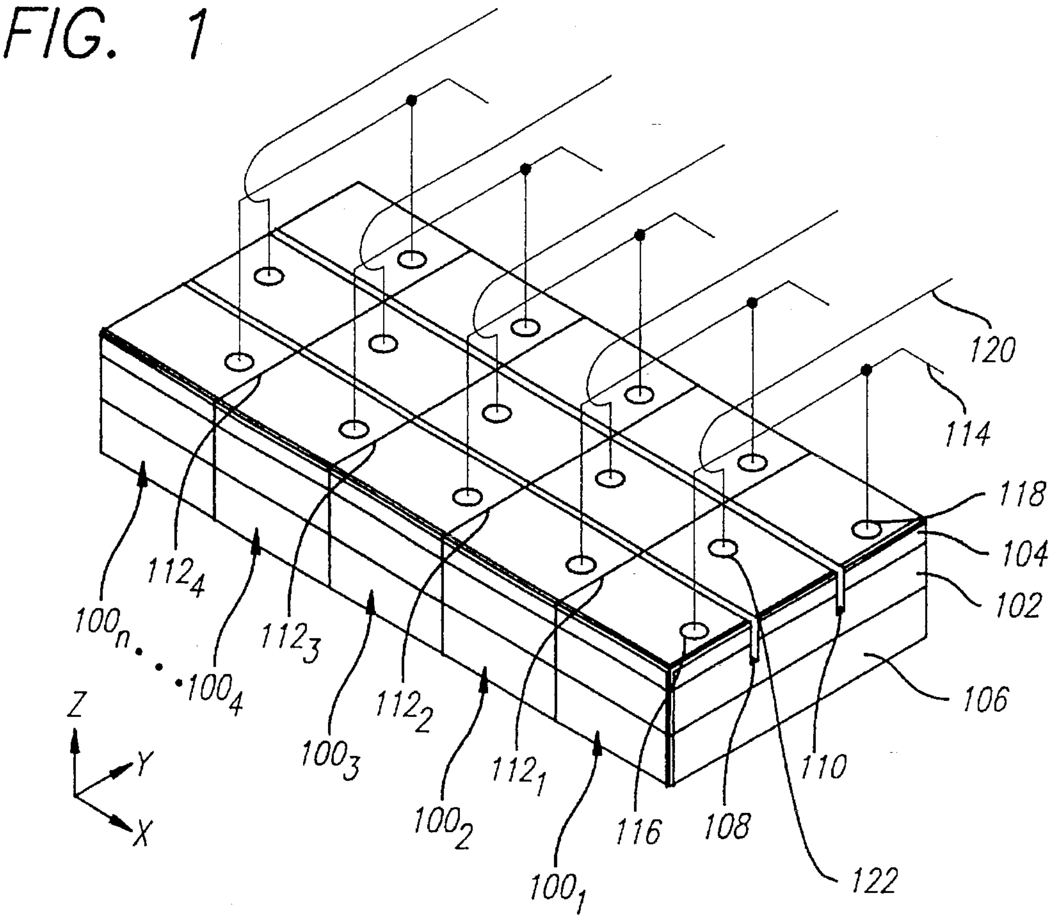
FIG. 1 is a simplified cut-away perspective view that illustrates the electrical interconnections of elements in a multi-dimensional ultrasonic transducer array according to the invention, with a backing layer and a flex layer removed.

FIG. 1 is a cut-away view of a portion of a 3×n ultrasonic transducer array according to the invention. For purposes of illustration, an X-Y-Z coordinate system is shown in FIG. 1 to define longitudinal, transverse, and vertical directions, respectively. Moreover, in order to make clear the general structure of the array, FIG. 1 does not show a backing layer and a flex layer, which are described below.

The array is divided in the longitudinal direction into n groups $100_1$, $100_2$, . . . , $100_n$ of three transversely formed piezoelectric elements. As is explained further below, the illustrated embodiment of the invention allows for a dual aperture. The invention is not limited, however, to groups that are three elements wide; rather, wider groups that allow for more than two apertures are also possible using the invention. Furthermore, the invention provides the same advantages for any number of elements in the longitudinal direction. In one prototype, the array was a 3×128 linear array, so that there were a total of 384 electrically and acoustically isolated elements.

The array includes a piezoelectric, ceramic layer 102. A conventional acoustic matching layer 106 is bonded to one side of the ceramic layer. A first electrically conductive layer 104, preferably nickel or gold, is sputtered or otherwise bonded or applied to the other side of the ceramic layer.

The matching layer may be of any conventional material. It is known to provide a matching layer on the piezoelectric layer of an ultrasound transducer and any conventional method may be used to do so. Note that FIG. 1 does not necessarily show the various layers to scale; actual layer thicknesses will depend on a given application and choice of materials and may be chosen using known techniques.

Parallel, longitudinal grooves 108, 110 are cut using known techniques into but preferably not through the ceramic layer 102. Each transducer group $100_1$, $100_2$, $100_n$, is thereby divided transversely into three elements—one center element and two outer elements. The array is also diced in the transverse direction along dicing lines $112_1$, $112_2$, $112_3$, $112_4$ so that the groups $100_1$, $100_2$, $100_n$ are electrically and acoustically isolated from each other in the longitudinal direction.

The dicing lines 112 (indices deleted) extend all the way through the ceramic layer 102 and conductive layer 104; longitudinal grooves 108, 110 extend through the first conductive layer 104. The portion of the grooves 108, 110 that extends into the ceramic layer 102, or at least through the conductive layer 104, can also be formed by masking or patterning during the deposition process, or by cutting after deposition. The separated portions of the conductive layer 104 in contact with each transducer element therefore form electrically isolated electrodes 210, 212, 214 for the respective elements.

Each transducer element of each group is electrically connected to conventional external timing, driving, sensing, conditioning, and beam-forming circuitry (not shown) via electrical leads or "interconnects." In a preferred embodiment of the invention, the two outer transducer elements of each group are activated as a pair and share a common interconnect 114, which is electrically connected at contact points 116, 118, to the electrodes of the respective elements. Another electrical lead or interconnect 120 is similarly provided for the center element of each group in order to connect it via a contact point 122 with the external circuitry. The metallization used to connect the elements to the external circuitry is referred to interchangeably below as "leads," "interconnects," or "traces," 114, 120, all of which are known, interchangeable standard terms in the context of ultrasonic transducers.

The first electrically conductive layer 104, of which the electrodes 210, 212, and 214 are portions, is preferably nickel or gold to allow for easy application (for example, by sputtering) and to provide good electrical contact and corrosion resistance. Other conductive metals may, however, also be used.

The way in which linear arrays of piezoelectric elements generate an ultrasonic beam when the driving circuitry applies electric signals via the interconnects, vias, and electrodes, is well known and is therefore not described further. The way in which the elements receive reflected acoustic energy and convert it piezoelectrically into electric signals that are passed along the same electrical paths as for transmission, is similarly well known.

FIG. 1 shows the leads 114, 120 extending vertically from the conductive layer for purposes of illustration only. Moreover, the leads of only one group are labelled, since the leads of other groups shown in FIG. 1 are arranged identically. Each group has corresponding leads. Furthermore, the actual leads will normally comprise electrically conductive traces (preferably of copper) that are patterned onto a flex layer (described below) as portions of a masked-on or etched-away second conductive layer. This is illustrated in other figures and is described below.

In the preferred embodiment, the outer elements of each group are electrically connected so that they are activated simultaneously. This is advantageous in that it allows for dual-aperture, wide-narrow operation of the transducer with a minimum number of traces and corresponding external connection points. When only the center elements of the array are activated, the elevation dimension (in the direction of the Y-axis) of the transducer is narrow, with near transverse focus. When the two outer elements and the center element are activated instead, the elevation dimension is wide, with far transverse focus. The array can be focused along two separate planes. Since the two outer elements are not operated independently in this embodiment, the array is of the type known as 1.5-dimensional.

It is, however, also possible according to the invention to provide separate leads for each element of each group, so that the array is of the type known as two-dimensional. As is explained in greater detail below, the invention makes these structures easier to manufacture than is possible using know techniques, since it makes it possible to pattern onto and otherwise use regions that normally cannot be used for the interconnects due to uncertainty in dicing widths.

Figure 2:
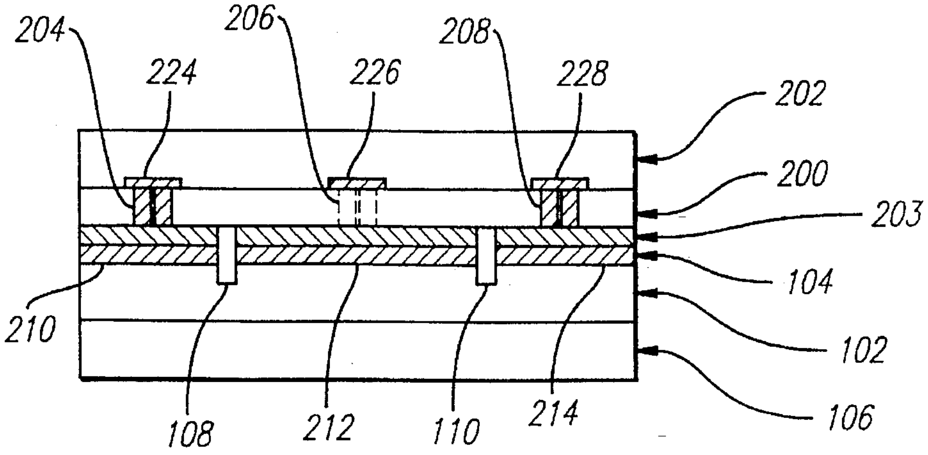
FIG. 2 shows a lateral cross section of the transducer according to the invention.

FIG. 2 is a cross sectional view of the transducer stack according to the invention taken along a plane that passes through the electrical contact points of the two outer elements. A flex layer 200 is provided to form the base for a flex circuit, which is described in greater detail below. A conventional backing layer 202, which is preferably molded, is bonded to the flex layer. Bonding using epoxy is preferred because of its strength.

A second electrically conductive layer 203 is applied to the flex layer 200 on the side opposite the backing layer 202. The second conductive layer may be applied in any conventional manner, for example, sputtering, electroplating and photolithography. The grooves 108, 110 extend through the second conductive layer so that, for each group of elements, it is separated into three portions, each of which forms an electrode that is in registration with the corresponding electrode 210, 212, 214 of the first conductive layer 104.

Conventional throughhole vias 204, 206, 208 extend through the flex layer 200 and are electrically connected with the portions of the conductive layer 203 that register with the electrodes 210, 212, 214, respectively. The via 206 for the center element is shown in phantom because it does not lie in line with the vias 204, 208 of the outer elements and is therefore not in the same cross-sectional plane. Each throughhole via is electrically connected with a corresponding one of the traces or leads 114 (for the outer elements) and 120 (for the center element) at contact points 224, 226, and 228.

The flex layer 200 is preferably made of a flexible, electrically non-conductive material with a suitable dielectric constant (which can be selected using well-known methods depending on the material and electrical properties of the other layers), and it should have a high anti-stretch modulus so as to allow for accurate and permanent positioning of the various patterned contact points, leads, and vias. The preferred material for the flex layer is two-sided Kapton since Kapton meets all of these requirements; furthermore, Kapton withstands high temperatures well, one can solder to it, it has low water absorption, and one can chemically etch the vias 204, 206, and 208 through it. Mylar and similar materials may also be used, but they will typically either not meet some of the requirements as well as Kapton, or they will require more complicated fabrication techniques to make the transducer according to the invention.

Since the preferred flex layer is two-sided Kapton, the electrically conductive layer 203 is preferably deposited on one side and the traces or leads 114, 120, and the contact points 224, 226, 228 (which may simply be portions of the traces) may be deposited on the other side. It is preferable to separate the electrodes and form the traces during processing of the first conductive layer on the flex layer using known masking or etching techniques. The portion of the grooves 108, 110 that extends through the conductive layer 203 can also be formed by photolithography or cutting after covering the underside of the flex layer with metallization. The flex layer is then bonded with the conductive layer against the ceramic layer 102 so that the separated electrode portions of the first and second conductive layers are in registration. The thickness of the conductive layer 203 will in typical applications be approximately 4–6 μm; the Kapton layer itself will typically be approximately 50–75 μm thick.

In order to provide full electrical isolation for the electrodes 210, 212, and 214 it is therefore not necessary to cut all the way through the Kapton layer. Rather, by patterning the electrodes, with separation, on one side of the flex layer and the traces on the other side, it is not necessary to cut the flex layer at all. This improves accuracy and eliminates fabrication steps. Even if the grooves 108, 110 are cut between the electrodes, however, they need only be cut to a depth equal to or just slightly greater than the thickness of the conductive layer 203. As is described below, not having to cut through the flex layer 200 allows for a smaller pitch for the array elements in the longitudinal direction.

The flex layer 200, the conductive layer 203, the contact points 224, 226, 228, the vias 204, 206,208, and the leads 114, 120 are preferably all fabricated as a single flex circuit 300. Once the electrodes (the separated second conductive layer 203) are patterned onto the one side of the flex layer 200, the leads are patterned onto the other side of the flex layer, and the vias are chemically etched through the flex layer, the flex circuit as a whole is then bonded onto the ceramic layer 102.

Note that it is not necessary to cut all the way through the ceramic layer 102 in order to form acoustically and electrically isolated array elements; rather, only the grooves 108, 110 and the dicing lines $\mathbf{112}_1$, $\mathbf{112}_2$, $\mathbf{112}_n$ (FIG. 1) need to be cut into the ceramic layer (through the first conductive layer 104). A single, longitudinally extending (in the X-direction) piezoelectric, ceramic piece is thus divided in the longitudinal direction (by dicing lines 112) and the transverse (Y) direction (by the grooves 108, 110) into three regions to form an array of n groups of ultrasonic elements. The ceramic layer can remain as a single piece.

FIG. 3 illustrates a view from above of two adjacent element groups in the array with the backing layer 202 (see FIG. 2) removed. In other words, FIG. 3 shows the layout of the side of the flex circuit 300 on which the leads 114, 120 are patterned. The grooves 108, 110 are shown by dashed lines since they do not extend to the surface and, indeed, ideally do not extend into the flex layer at all (although the second conductive layer 203 must be separated into electrically separated electrode portions, but preferably by patterning them by a sputtering or photolithographic process.)

The dicing line 112 is shown by a dash-dotted line in FIG. 3 since it is similarly not necessary to cut through or even into the top surface of the non-conductive flex layer 200 in order to ensure proper electrical isolation of adjacent elements in adjacent groups. The electrode portions of the second conductive layer are preferably separated into groups by the dicing operation (by cutting at most only partially into the undersurface of the flexible base layer 200), to ensure proper registration. This increases the space available for laying out electrically conductive traces while avoiding possible short-circuiting caused by the statistical process variation in width or, alternatively, allows for smaller transducer elements with good separation between conductive traces and vias.

In FIG. 3, the following geometric characteristics are labelled:

w: the pitch of the array groups. In one prototype of the invention the pitch w was 300 μm (12 mil);

t: the width of the conductive traces or leads 114, 120, which is preferably at least 50 μm (2 mil) to ensure reliable fabrication using known deposition techniques and robustness to the transducer manufacturing process;

s: the separation between each throughhole via 226 and the nearest trace to which it is not supposed to be connected; s is preferably at least 75 μm (3 mil) in order to avoid random shorts between the vias and traces;

v: the diameter of a via, which is preferably no greater than about 75 μm (3 mil); and e: the margin of uncertainty or inaccuracy in cutting the dicing line using known technology. Recall that it is not necessary to cut the dicing line into the flex layer 200 according to the invention.

Using conventional dicing technology, there is an uncertainty of as much as 100 μm (4 mil) in the placement of the dicing line 112, which includes the total dicing cut width plus the uncertainty in placement of the cut. The actual dicing line 112 could therefore lie anywhere between approximate limit lines 302, 303 and without the non-diced flex layer according to the invention, it would not be possible to locate any portion of vias or traces between these limit lines 302, 303. Using the invention, therefore, one does not need to worry about the location of the dicing line when laying out the traces 114, 120, since the dicing line does not interrupt the flex circuit's upper surface, on which the traces are patterned.

It is furthermore not necessary for the traces 114, 120 to extend off of opposite sides of the transducer, although this will usually make electrical connection to the external driving circuitry easier since the distance between adjacent connections is then greater. All traces or leads could instead extend from the same side of the flex circuit.

Neither is it necessary for the two outer elements to be electrically connected for simultaneous activation. This arrangement is advantageous for creating a dual-aperture array, since it reduces the number of separate traces and corresponding external connections to the traces, and since the outer elements will need to be activated simultaneously anyway.

FIG. 4 illustrates a trace layout that provides for independent activation of all the elements in a group via the center trace 120 (for the center element) and outer traces 414, 416, for the respective outer elements. The three separate traces can be patterned onto the flex layer 200 using the same known techniques as are used in the embodiment shown in FIG. 2. For the purposes of illustration, only one group is shown; other groups will have the same trace layout. Notice that, even in this case, there is no need to run more than one trace between any via and any edge of the group. As such, the independently activated elements provide the same advantage (freedom from space restrictions imposed by uncertainty in the position of dicing lines) as does the near-far or wide-narrow aperture embodiment shown in FIG. 3, in which the outer elements are connected to a common trace 114.

The embodiment shown in FIG. 4 is suitable for providing both a 1.5- and two-dimensional array, with different, transversely shifted beam planes. For 1.5-D operation, either the center element is activated, or the outer elements are activated simultaneously. Using the embodiment shown in FIG. 4 for 1.5-D, wide-narrow aperture operation would require the additional connection between the additional trace and the driving circuitry, but it would allow the single array to be used selectably for both modes of operation (1.5- and 2-D).

FIG. 5 shows one element of a 5×n array using a double flex layer construction 500 according to the invention. The structure and fabrication of this 5×n array is generally the same as for the 3×n array described above. One exception, however, is that each group is separated in the transverse direction by four grooves (indicated by dashed lines)in the ceramic layer and conductive layer into a center element 501, two intermediate elements 502, 504, which are adjacent to the center element on either side, and two outer elements 506, 508, which are adjacent to the intermediate elements on either side. Traces 520 and 514 are patterned as before onto the upper surface of the flex layer so as to connect the center and outer elements, respectively, to external, conventional driving circuitry (not shown). Also as before, the traces are connected to the electrodes (which are patterned into the second conductive layer 203 on the underneath side of the bottom flex layer of the flex layer construction 500) by means of conventional vias, which are indicated as circles.

Another exception is that, in the embodiment shown in FIG. 5, two sheets of flexible material are used to form a two-layer flex construction, in which traces are patterned onto the upper surface of each layer. The two layers may be joined together using any conventional adhesive or bonding technique that is suitable for the material, such as Kapton, that is chosen for the flex layers. The second electrically conductive layer 203, which is in contact with the first conductive layer 104, is deposited onto the underneath surface of the bottom flex layer. Traces 514 and 520 are patterned onto the upper surface of the upper layer as in the previously described embodiments. A trace 522 (shown by dashed lines) that connects the intermediate elements 502, 504 is patterned onto the upper surface of the underneath flex layer. Vias (shown as dashed circles) connect the trace 522 to the electrodes (separated portions of the conductive layer) under the two-layer flex construction.

The dice lines separating the ceramic elements are indicated in FIG. 5 as dashed lines perpendicular to the traces. Note that these cuts do not actually extend into either layer of the flex construction, but are included in FIG. 5 to show the separation between the elements. The five-wide embodiment shown in FIG. 5 allows for three separate aperture widths (narrow, intermediate, wide) depending on which element or element groups are activated. One advantage of the invention in this three-aperture embodiment is, as before, that patterning the traces and electrodes onto the un-diced flex layer construction to form a single flex circuit not only makes for ease of fabrication and assembly, but it similarly allows for better use of the surface area of the flex layer when laying out the traces.

The idea of multiple flex layers joined to form a single flex construction can be extended to greater than two layers, so that arrays even wider than five elements can be implemented according to the invention. In such case, traces will be patterned onto the upper surface of each layer and the underside of the bottommost layer will have the conductive layer deposited onto it.

FIG. 6 illustrates a 5×n, two-dimensional embodiment of the invention that uses only a single flex layer 600. The structure and fabrication of this 5×n, 2-D array is generally the same as for the 3×n array described above, with the exception that each group is separated in the transverse direction by four grooves (indicated by dashed lines)in the ceramic layer and conductive layer into a center element 601, two intermediate elements 602, 604, which are adjacent to the center element on either side, and two outer elements 606, 608, which are adjacent to the intermediate elements on either side. One trace 620 is patterned onto the upper surface of the flex layer so as to connect the center element 601 to external, conventional driving and sensing circuitry (not shown). Traces 614, 616, also patterned on the upper surface of the flex layer, electrically connect the intermediate elements 602, 604, respectively, to the external circuitry. As before, the traces are connected to the electrodes (which are patterned on the underneath side of the flex layer construction 500) by means of conventional vias, which are indicated as circles 624, 626, 628.

The outermost elements 606 and 608, however, do not need vias through the flex layer for connection between the external circuitry and the corresponding electrodes. Rather, traces 630, 632 (or other conventional conductors, may be connected directly to the corresponding electrodes formed on the underside of the flex layer 600. Each array element can therefore be stimulated independently of the others (thereby providing 2-D capability) with a single flex circuit, while still ensuring proper distance between each trace and via, and between each via and trace and the nearest dice line.

One advantage of the invention is that, regardless of the embodiment (even the multi-flex layer embodiments), there is never a need to run more than one trace between any via and any edge of a transducer element group. This is not, however, necessary: as long as one is willing to accept wider groups (for example, for low-frequency applications, then more than one trace may be led between a via and an edge. Even in these arrangements, the invention allows for more usable space. Another advantage of all embodiments of the invention is that the flex circuit (singular or as a multi-layer construction) and the ceramic layer can be fabricated as units and easily assembled into a transducer, thanks to the ease of registration of the units along the groove portioned diced into the ceramic layer and patterned or cut into the electrode side of the flex circuit.

We claim:

1. An ultrasonic transducer array comprising:

A. a piezoelectric ceramic layer separated in a longitudinal direction into n transducer groups, with each group separated in a transverse direction into m transducer elements;

B. a flex circuit that includes:

1) a flexible, electrically non-conductive base layer;

2) for each transducer element, an electrically conductive via through the base layer in electrical contact with the respective transducer element;

3) an electrically conductive layer, on a bottom side of the flex circuit, that is divided into a plurality of flex circuit electrodes, with each flex circuit electrode being in electrical contact with a respective one of the transducer elements; and 4) for each group, electrically conductive traces that are electrically connected by vias to predetermined ones of the flex circuit electrodes and to external driving circuitry, and are located on a top side of the flex circuit in which the electrically conductive layer, and thus the flex circuit electrodes, as well as the electrically conductive traces and vias are pre-patterned onto the flexible base layer, the flex circuit thereby forming a pre-patterned, pre-aligned unit.

2. An ultrasonic transducer array as defined in claim 1, in which at most two traces are located on the top side of the flex circuit for each group, measured in the longitudinal direction.

3. An ultrasonic transducer array as defined in claim 2, in which:

A. each transducer group has three elements—a center element and two outer elements; and B. the two outer elements are electrically connected by a single trace.

4. An ultrasonic transducer array as defined in claim 2, in which, measured in the longitudinal direction:

A. each array group is no wider than 300 μm;

B. each trace is at least 50μm; and

C. the separation between each via and the nearest trace which is not connected to it is at least 75 μm.

5. An ultrasonic transducer array as defined in claim 2, in which:

A. each transducer group has three elements—a center element and two outer elements; and B. each group has three traces and each element is electrically connected to and independently stimulated over a different one of the traces.

6. An ultrasonic transducer array as defined in claim 1, in which:

A. the transducer groups each contain more than three elements;

B. the flex circuit includes a plurality of flexible, electrically non-conductive base layers;

C. the electrically conductive vias extend through all the base layers and are in electrical contact with the respective transducer element;

D. the electrically conductive traces are located on a top surface of each base layer; and E. at most two traces are located on the top surface of any base layer for each group, measured in the longitudinal direction.

7. An ultrasonic transducer array as defined in claim 1, in which:

A. each transducer group has five elements—a center element, two intermediate elements, and two outer elements;

B. separate traces are provided for the center element and the outer elements of each group;

C. vias are provided only for the center element and the intermediate elements;

D. the outer elements have separate traces that directly connect the flex circuit electrodes for the outer elements with the external circuitry and are located entirely off of the top surface of the base layer;

E. at most two traces are located on the top surface of the base layer for each group, measured in the longitudinal direction; and F. each of the five elements in each group is thereby provided for independent stimulation over a respective trace.

* * * * *